United States Patent [19]

Glassberg

[11] Patent Number: 5,593,832
[45] Date of Patent: Jan. 14, 1997

[54] METHOD FOR FORENSIC ANALYSIS

[75] Inventor: Jeffrey Glassberg, Chappaqua, N.Y.

[73] Assignee: Lifecodes Corporation, Stamford, Conn.

[21] Appl. No.: 376,487

[22] Filed: Jan. 23, 1995

Related U.S. Application Data

[63] Continuation of Ser. No. 931,482, Aug. 19, 1992, abandoned, which is a continuation of Ser. No. 150,465, Feb. 2, 1988, abandoned, which is a continuation-in-part of Ser. No. 582,334, Feb. 22, 1984, abandoned, which is a continuation-in-part of Ser. No. 468,113, Feb. 28, 1983, abandoned.

[51] Int. Cl.⁶ ............................. C12Q 1/68; C12N 15/70; C07H 21/04
[52] U.S. Cl. ......................... 435/6; 435/320.1; 536/24.3; 536/24.31
[58] Field of Search .................. 435/6, 320.1; 536/24.3, 536/24.31

[56] References Cited

U.S. PATENT DOCUMENTS

| | | | |
|---|---|---|---|
| 4,302,204 | 11/1981 | Wahl et al. | 436/501 |
| 4,358,535 | 11/1982 | Falkow et al. | 435/5 |
| 4,582,788 | 4/1986 | Erlich | 435/6 |

FOREIGN PATENT DOCUMENTS

| | | | |
|---|---|---|---|
| 0076123 | 4/1983 | European Pat. Off. . | |
| 0079139 | 5/1983 | European Pat. Off. . | |
| 84796 | 8/1983 | European Pat. Off. | C12N 15/00 |
| 0133288 | 2/1985 | European Pat. Off. . | |
| 0133671 | 3/1985 | European Pat. Off. . | |
| 8303260 | 9/1983 | WIPO | C12Q 1/68 |
| WO84/03715 | 9/1984 | WIPO . | |
| WO84/04758 | 12/1984 | WIPO . | |

OTHER PUBLICATIONS

Giusti et al., "Application of deoxyribonucleic acid (DNA) polymorphisms to the analysis of DNA from sperm" J. Forensic Sci. 31:409–417.
Kanter et al., "Analysis of restriction fragment length polymorphisms in deoxyribonucleic acid (DNA) recovered from dried bloodstains" J. Forensic Sci. 31:403–408.
DeMartinville, B. et al. (1982). "Assignment of the First Random Restriction Fragment Length Polymorphism (RFLP) Locus (D14S1) to a Region of Human Chromosome 14," Am. J. Hum. Genet. 34:216–226.
Goodburn, S. E. Y. et al. (1984). "Allelic Variation and Linkage Properties of a Highly Polymorphic Restriction Fragment in Humans," Mol. Biol. Med. 2:233–238.
Lamppa, G. A. and Bendich, A. J. (1981). "Fine Scale Interspersion of Conserved Sequences in the Pea and Corn Chloroplast Genomes," Mol. Gen. Genet. 182:310–320.
Bishop et al. (1980) Cancer Incidents in Defined Populations, Bambury Report No. 4, Cold Spring Harbor Lab:421–433.
Kan, Y. W. and Dozy, A. M. (1978). Proc. Nat. Acad. Sci. USA 75:5631–5635.
Kurnitt, D. M. and Hoehn, H. (1979). Ann. Rev. Genet. 13:235–258.
Lewin, R. (1981). Science 211:690–692.
Davies, K. E. (1981). Hum. Genet. 58:351–357.
Owerbach, D. et al. (1982). The Lancet, vol. 1:800–883.
Balazs, I. et al. (1982). Proc. Nat. Acad. Sci. USA 79:7395–7399.
Proudfoot, N. J. et al. (1982). Cell 31:553–563.
Erlich, H. A. et al. (1983). Science 222:72–74.
Schmidtke, J. et al. (1983). Forensic Science International 23:43.
Humphries, P. et al. (1983). Mo. Gen. Genet. 190:143–149.
Harris, S. E. et al. (1983). Proc. Nat. Acad. Sci. USA 80:6460–6464.
Cooper, D. N. and Schmidtke, J. (1984). Hum. Genet. 66:1–16.
DNA Sequence Variants in the gamma– gamma, – delta – and beta–Globin Genes of Man, Jeffreys, A. J., Cell 18:1–10 (1979).
A Note on Positive Identification of Paternity by Using Genetic Markers, Majumder, P. P. et al., Hum. Heredity 33:29–35 (1983).
Cancer Incidence in Defined Population "Banbury Report No. 4," Eds., John Cairns et al., Cold Spring Harbor Res., pp. 421–433 (1980).
Probability of Paternity, Salmon, D. and J. Brocteur, Amer. J. Hum. Gent. 28:622–625 (1976).
Probability of Paternity Exclusion in Different Mother–Child Genotype Combinations, Ryman, Nils et al., Hereditas 94:99–104 (1981).
Exclusion of Paternity: The Current State of the Art, Chakraborty, R. et al., Amer. J. of Hum. Genetics 26:477–488 (1974).
Exclusions and Attributions of Paternity: Practical Experiences of Forensic Genetics and Statistics, Valentin, J., Amer. J. of Hum. Gent. 32:420–431 (1980).
Mechanism of Activation of a Human Onogene, Tabin, C. J. et al., Nature 300:143–149 (1982).
Isolation and Preliminary Characterization of a Human Transforming Gene from T24 Bladder Carcinoma Cells, Goldfarb, et al., Nature 296:404–409 (1982).
Genome Instability in a Region of Human DNA Enriched in Alu Repeat Sequences, Calabretta, B. et al., Nature 296:219–225 (1982).
The Highly Polymorphic Region Near the Human Insulin Gene is Composed of Simple Tandemly Repeating Sequences, Bell, G. I. et al., Nature 295:31–35 (1982).
A Highly Polymorphic Locus in Human DNA, Wyman, A. R. et al., Proc. Nat'l Acad. Sci., USA 77(11):6754–58 (1980).
Construction of a Genetic LinKage Map in Man Using Restriction Fragment Length Polymorphisms, Botstein, D. et al., Amer. J. Hum. Genetics, 32:314–331 (1980).

Primary Examiner—Mindy Fleisher
Assistant Examiner—Scott D. Priebe
Attorney, Agent, or Firm—Venable, Baetjer, Howard & Civiletti, LLP

[57] ABSTRACT

This invention relates to a method for identification of samples collected as physical evidence for forensic analysis. The identification is based upon an analysis of DNA length polymorphisms generated by the action of restriction endonucleases.

4 Claims, 1 Drawing Sheet

METHOD FOR FORENSIC ANALYSIS

CROSS REFERENCE TO RELATED APPLICATIONS

This application is a continuation of application Ser. No. 07/931,482, filed 19 Aug. 1992, now abandoned, which is a continuation of application Ser. No. 150,465, filed Feb. 2, 1988, now abandoned, which is a continuation-in-part of application Ser. No. 582,334, filed Feb. 22, 1984, now abandoned, which is a continuation-in-part of application Ser. No. 468,113, filed Feb. 28, 1983, now abandoned.

FIELD OF THE INVENTION

This invention relates to a new and improved diagnostic test applied to the determination of paternity and for the establishment of individual genetic identity. It should be noted that although, as is the practice in the art, a test is referred to as a paternity test; there is nothing which precludes its employment in cases of disputed maternity.

BACKGROUND OF THE INVENTION

There are numerous situations when the ability to determine an individual's identity is of importance; for example, the matching of physical evidence left at the scene of a crime with a particular suspect, the establishing of the identity of an individual in relation to his/her mother or father as in the determination of paternity or more generally when establishing the genetic identity of a strain of a virus, bacterium, alga, fungus, plant or animal. Some of the tests employed for such determinations rely upon the identification of polymorphic proteins in the plasma, from the surface, or extracted from within the cells of the individuals in question.

The well known human ABO blood group substances may be used by way of explanation. The ABO blood group substances are carbohydrate in composition and are synthesized by enzymes which are the products of a single human gene. One form of the gene (the A allele) produces an enzyme used in the synthesis of A-type blood, while another form of the gene (the B allele) produces an enzyme used in the synthesis of B-type blood. The absence of both alleles 1 results in the production of O-type blood, while the presence of both alleles results in the production of AB-type blood. The ABO substances possess antigenic properties and may be detected immunologically by reaction with the appropriate antisera. It is the differential reactivity of these substances with said antisera which forms the basis of the A, B, O and AB blood type groupings.

If everyone possessed the same blood type, the substance would be useless in discriminating among individuals. The fact that the blood group substances exist in several forms (i.e., are polymorphic) allows for discrimination. However, in terms of its power to exclude, as in cases of disputed paternity, not only is the number of different alleles important, but also the frequencies with which those alleles occur. Since these allele frequencies vary among populations, the efficacy of exclusion also varies. The power of a test to exclude is represented by its exclusion capability, a numerical value ranging from 0 to 1.0. The exclusion capability of the ABO system among American blacks is 0.1774 while among American Caucasians it is 0.1342. The exclusion capability increases to 0.1830 for Swedes and to 0.1917 for Japanese.

One approach to increase the exclusion capability has been to expand the analysis to include other polymorphic substances. In Sweden, twelve polymorphic substances are analyzed. The overall exclusion capability of this battery of tests approaches 0.870. The addition of more systems to the set, even if highly informative, will not increase the cumulative probability greatly, once the number of systems already involved is large. A survey of 25 systems based on immunological tests (Antigen-Antibody reactions) revealed a cumulative probability of non-paternity of 0.7694 while a similar analysis of 32 systems based on biochemical tests (enzyme reactions or electrophoretic mobility) yielded a value of 0.9512. The combined 57 systems still only yielded an exclusion value of 0.9887. Extensive investigations are not practical in terms of a paternity testing program since many of the systems, because of cost, paucity of reagents, technical complexity, low reliability, and/or insufficient experience are not considered suitable for routine work.

It is well known in the forensic sciences to employ multiple test systems for the determination of identity. For example, in addition to the ABO blood group antigens, MN and Rh antigens are also analyzed. If the test sample is liquid Le and Se antigens may also be included. Three red blood cell enzymes acid phosphatase, phosphoglucomutase, and esterase D are examined for the presence of electrophoretic variants. Finally, tests for serum proteins such as haptoglobins are also employed. As was the case for the determination of paternity, the extent of these forensic investigations is also limited by cost, technical complexity and low reliability.

The above practical considerations not withstanding, a more serious theoretical problem plagues all of the existing tests. Since the tests are based on the analysis of a protein or its activity, it is the gene product and not the gene itself which is the subject of the investigation. In accord with the instant inventions disclosed hereinafter, it is preferable to analyze the gene directly rather than the product of its expression, in situations where paternity is of interest, because of the degeneracy that is inherent in the process by which genetic information is expressed.

The flow of genetic information in cells is well known. The information directing the biosynthesis of any protein is encoded in the sequences of DNA nucleotides known as a gene. The DNA of the cell may be viewed as the storage form of the genetic information. The DNA molecules are large, chemically stable, easily replicated and contain many gene sequences. For example, the entire genetic repertoire of the bacteria $E.$ $coli$ is contained in a single DNA molecule composed of approximately $4.2 \times 10^6$ nucleotide base pairs.

Transcription is the process by which the retrieval of information is begun. Transcription involves the resynthesis of the information in the form of a nucleic acid called RNA. One type of RNA, messenger RNA (mRNA), transports the information to the site of protein synthesis called ribosome.

Once the mRNA is synthesized from the gene the process of protein synthesis may begin. This process is essentially one of molecular decoding, in which the nucleotide sequence of the mRNA provides a template for the synthesis of a particular protein. Since there is a change from a nucleic acid language into that of a protein language, this process of protein synthesis appropriately is referred to as translation. Continuing the analogy a bit further, it would be appropriate to think of the constituents of the nucleic acids, the nucleotides, as representing the alphabet of the nucleic acid language and the amino acids, the building blocks of proteins, as representing the alphabet of the protein language.

During the process of translation not only are the languages changing but the alphabets are changing as well. This is a particularly complex process which is known to involve over 100 types of molecules. As the mRNA is passed through the ribosome (much like the tape through a tape recorder) groups of 3 nucleotides (codons) are positioned such as to orient accessory RNA molecules, known as transfer RNA (tRNA), carrying a single amino acid into the proper alignment for the addition of the amino acid to the growing protein chain.

Of special interest with respect to the subject invention is the coding ratio of nucleotides to amino acids. As mentioned above this ratio is three nucleotides coding for one amino acid. Since it is necessary to code for twenty different amino acids uniquely with the available four types of nucleotides (A, U, G, C), three represents the minimum acceptable ratio. A coding ratio of one nucleotide to one amino acid would only accommodate four of the twenty amino acids necessary for protein synthesis. A coding ratio of two yielding 16 ($4^2$) combinations likewise falls short of the required complexity. However, with a coding ratio of three, 64 ($4^2$) different combinations are possible. This excess of twenty code words confers upon the genetic code a condition known as degeneracy. A degenerate code contains several different code words for the same amino acid. The situation does not exist, however, where one code word would specify two different amino acids. The code may be degenerate, but it is not ambiguous.

Knowing the sequence of nucleotides of a messenger RNA, it is possible to explicitly write the sequence of amino acids coded therein, but the reverse is not true. Because of the degeneracy of the genetic code, a number of nucleotide sequences would be consistent with a given amino acid sequence. For example, consider the fragments of a mRNA from the same gene in two different individuals "A" and "B".

BRIEF DESCRIPTION OF THE INVENTION

The object of this invention is to provide a new and improved test for the determination of paternity in sexually reproducing organisms and to establish individual genetic identity. These objectives are achieved by analyzing the DNA of said organism in respect to one or more polymorphic genetic regions, differentiating the polymorphisms in terms of relative size of the genetic regions and by so doing characterize an individual member of the species.

In one embodiment, DNAs derived from the offspring, the mother and for example the putative father are separately digested with one, or more, restriction enzymes and the resulting fragments are separated on the basis of size by causing them to migrate through a gel matrix under the influence of an electric current. The polymorphisms are detected by hybridizing the above-treated DNAs with labelled (e.g., radioactive) "probe" DNAs.

The probe DNAs are variable DNA fragments that have been joined to a vector DNA which is able to replicate in a host cell (e.g., plasmid pBR322, bacteriophage lambda or M13 in *Escherichia coli*, or SV40 in monkey cells) and then purified from the host cells.

The reacted probe DNAs allow visualization of the position, and thus the sizes, of the DNA fragments of the offspring, the mother, and the putative father, whose sequences are homologous to those of the probe DNAs. Because the probe DNAs have been chosen on the basis of their being one allele from a polymorphic locus, the sizes of the DNA fragments homologous to those of the probes will vary among individuals.

All DNA fragments possessed by the offspring will be derived from either the offspring's mother or father, barring mutations or certain other rare events. A comparison of the sizes of the DNA fragments detected by the probe DNAs thus allows one to determine whether or not the putative

|  | INDIVIDUAL "A" | INDIVIDUAL "B" |
| --- | --- | --- |
| mRNA | [UUC CCC CGA GUU CUA AAG] | [UUU CCG AGG GUC CUU AAG] |
| protein | [phe-pro-arg-val-leu,lys] | [phe-pro-arg-val-leu-lys] |

An analysis of the protein would indicate the two individuals are identical, whereas an analysis of the mRNA sequence would indicate clear differences. Any paternity test based on a protein analysis be it either immunological or biochemical would fail to distinguish between the two individuals. A test based on the analysis of the genetic material, either RNA, or preferably DNA, would allow such a distinction to be made.

Although the discussion above has centered on determination of paternity in humans it should be kept in mind that such tests, given the appropriate reagents, may be extended to include certain other animal species (e.g., horses, cows, dogs, etc.). In reference to the subject invention, because of the unique approach taken therein, the test procedure is applicable to a determination of parentage in any group of sexually reproducing organisms including plants as well as animals.

In a further application of the subject invention, the genetic identity of individuals may be established. This application is particularly useful in the area of forensic science or for the identification of strains of microorganisms, plants or animals.

father could be the biological father. For example, if the offspring's DNA yields a 8600 base-pair fragment homologous to one of the probe DNAs, and if the mother's DNA lacks this fragment, then the biological father's DNA must contain it. If the putative father's DNA lacks this fragment he can be excluded as the biological father.

In a further embodiment, samples of DNAs derived from a suspect and from physical evidence (blood, skin, sperm, etc.) at a crime scene may be compared by the use of the probes described above to establish identity between the samples and the suspect. Thus the DNA polymorphism with respect to the hybridization assay provides the forensic scientist with a "molecular fingerprint" to be included along with the rest of the analysis of physical evidence.

In yet another embodiment, a sample of DNA derived from an individual is compared with that DNA derived from other members of a strain of organism on the basis of relative size for the purpose of establishing the strain identity of said individual.

DETAILED DESCRIPTION OF THE INVENTION

Figure 1:
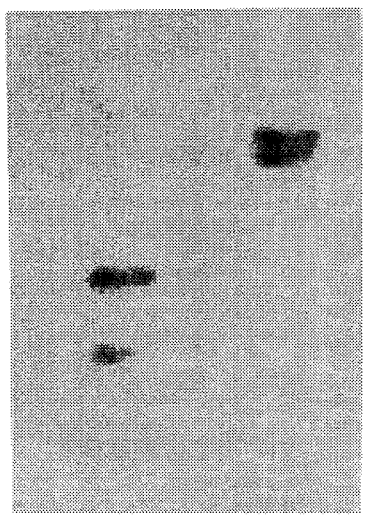
FIG. 1 represents the autoradiograph described in Example VII.

In one of its embodiments, the instant invention consists of the four interrelated steps of: DNA isolation and restriction; gel electrophoresis and DNA blotting; hybridization and washing; and finally autoradiography.

DNA Isolation and Restriction

The isolation of DNA from cell samples is carried out by art recognized procedures. DNA preparation involves cell lysis, sodium dodecyl sulfate and sodium perchlorate, chloroform/isoamylalcohol extractions, and ethanol precipitation.

Following its preparation each DNA sample is subjected to analysis with one or more restriction endonucleases. Restriction endonucleases are enzymes which recognize short specific sequences of about 4–7 nucleotide base pairs and cleave the DNA at or near these sites. Although there are more than 200 restriction enzymes from which to choose, the selection of any particular enzyme to employ in the test would depend on the type of sample DNA, the number of fragments required and the availability and cost of the reagents.

The human genome, which consists of approximately $6 \times 10^9$ base pairs of DNA, would be cleaved into $10^6$ to $10^7$ discrete fragments ranging in size from $10^2$ to $10^5$ base pairs by a single restriction endonuclease. The complexity of such a digest is a reflection of the number and location of the endonuclease specific cleavage points within the sample DNA. An exhaustive identification of each fragment from parallel treatments involving a number of different endonucleases would, in theory, result in a "molecular fingerprint" which would be unique for each human being. Although theoretically possible, such a detailed analysis is impractical. The subject invention overcomes this problem by permitting the analysis of a subset of the existing cleavage products. Employing the jargon of the genetic engineer's art, one is said to "probe" the existing cleavage products for the existence of the unique nucleotide sequence of interest. One well known method for accomplishing this analysis is the technique of Southern blotting.

Gel Electrophoresis and Blotting

According to the method of Southern (J. Mol. Biol. 98:503–17 (1975)) the double stranded DNA fragments obtained from the treatment with the restriction endonuclease are separated by size by electrophoresis in an agarose gel, and the DNA made single stranded by soaking the gel in alkali. The gel is placed flat onto a "wick" of filter paper that connects with a trough containing concentrated salt solution.

A single sheet of cellulose nitrate is then placed on top of the gels and a large stack of dry absorbent paper towels laid flat on top of the cellulose nitrate. The salt solution is drawn up by the absorbent paper towels, passing through the gel and cellulose nitrate sheet. As the solution passes through the gel, the single stranded DNA will be leached from the gel and pass onto the cellulose nitrate filter. Cellulose nitrate has the property of binding single-stranded DNA, so all the DNA will be leached from the gel and pass onto the cellulose nitrate filter. Cellulose nitrate has the property of binding single-stranded DNA, so all the DNA will adhere to this support. The end result of this procedure will be a perfect replica of the DNA from the original agarose gel, but the DNA is now single-stranded and immobilized on the cellulose nitrate filter sheet. The DNA size pattern from the original agarose gel is, nevertheless, faithfully preserved. Fragment sizes may be calibrated by comparison to marker DNA of known sizes.

Hybridization and Washing

A hybridization reaction is said to occur when two single-stranded DNAs from different sources reassociate to form a double-stranded DNA owing to complementary base pairing between the two interacting strands. DNA/RNA hybrids may also be formed by means of the analogous associations.

With respect to the subject invention a DNA/DNA hybridization is performed. One contributory source of material for the hybridization reaction is the single-stranded DNA present in the Southern blots of the restriction fragments. The other sources of hybridizing strands are the so-called "probe" DNAs. These DNAs represent variable DNA fragments chosen on the basis that they represent sequences corresponding to one allele of a polymorphic gene locus. A full description of the isolation and characterization of the "probes" is presented in a subsequent section of this disclosure.

A variety of hybridization conditions are recognized in the art including 50 percent formamide at 40°–50° C. or moderate salt at 65°–68° C. Dextran sulfate may be used to enhance the rate of reassociation. After hybridization, the filters are washed extensively for remove background (unhybridized) probes. The washing procedure is carried out at elevated temperature and reduced salt concentrations to remove non-specific DNA/DNA hybrids as well.

Preparation of Probe DNAs

As mentioned previously, the probe DNAs represent variable DNA fragments, chosen on the basis that they represent one-allele of a polymorphic genetic region. In this context the polymorphism is one of length. The variability in fragment length is a result of a difference in the number and/or location of endonuclease restriction sites which were attacked during the generation of the fragments. Thus, if all individuals possessed a DNA fragment of similar size which hybridized to the probe DNA, the region would be considered monomorphic and of little utility with respect to the subject invention. Whereas when individuals possess DNA fragments of different sizes which hybridize with the probe DNA fragment; then that fragment can be said to represent an allele of a genetic region which displays size polymorphism. The evaluation of probes is then of critical importance and may be considered to consist of the two interrelated steps of probe generation and probe identification.

Probe Generation

The generation of probes may be accomplished according to art recognized procedures for the construction of a collection of cloned DNA fragments. The steps normally include: digesting a DNA sample with a specific endonuclease, recovering fractions of DNA of appropriate size from the digest, precipitating the fragments, introducing the fragments in to an appropriate cloning vector, transforming a competent host organism with the vector, and recovering colonies containing the cloned probe DNA. A variety of endonucleoases and vectors exist which may be used in the generation of probes. The methods for accomplishing the cloning is well known in the art (see for example, *Molecular Cloning: A Laboratory Manual*, T. Maniatis, et al., Cold Spring Harbor Lab 1982). Two human DNA probes generated in such a manner are pAW 101 and pLM 0.8. Samples of *E. coli* harboring pAW 101 and pLM 0.8 were deposited with The American Type Culture Collection, 12301

Parklawn Drive, Rockville, Md. on Feb. 8, 1984 where they were assigned the accession numbers ATCC 39605 and ATCC 39604, respectively and the requisite fees were paid. Access to the cultures will be available during the pendency of the patent application to one determined by the Commissioner to be entitled thereto under 27 C.F.R. §1.14 and 35 U.S.C. §122. All restrictions on availability of said culture to the public will be irrevocably removed upon the granting of the instant application and said culture will remain permanently available during the term of said patent. Should the culture become nonviable or be inadvertently destroyed, it will be replaced with viable culture(s) of the same taxonomic description.

Alternatively, cDNA probes may also be employed. These probes are generated initially from RNA by a reverse copying procedure and is detailed in Example II herein or EPO Publication No. 0 084 796.

Irrespective of the method used to generate the probes, once obtained, each probe must be evaluated for usefulness in the testing procedure.

Identification of Useful Probes

To evaluate the efficacy of a particular probe from the collection of probes generated above, DNA is isolated from four different individuals and separately digested with a restriction endonuclease. These DNAs are subjected to agarose gel electrophoresis, running a mixture of three of the individuals' DNAs in one lane and a sample from the fourth individual in an adjacent second lane. The electrophoresed DNAs are blotted as described previously. Single-stranded DNA is isolated from an individual clone selected from the group of potential probes containing clones generated above. The probe DNA is labelled and used to hybridize with the electrophoresed DNA of the four individuals. If the tested probe yields more bands in the lane with the three individuals' DNAs than in the lane with the one individual's DNA, it becomes a candidate to detect polymorphisms. Probes identified by the foregoing procedure are further tested by hybridization against a sufficiently large population of test individuals to effectively determine the extent of polymorphism. Probes corresponding to regions with at least four different alleles present in the population with frequencies greater than 10% each are incorporated into the test.

According to a preferred embodiment of the invention, a collection of polymorphic probes are employed rather than the reliance on a single polymorphic probe. This use of multiple probes increases the sensitivity of the test dramatically. For example, if ten different probes are employed and each probe identifies a polymorphic region consisting of eight equally frequent occurring alleles, approximately a million individuals could be uniquely identified.

The parameters to be evaluated when selecting a particular probe for inclusion in the collection comprise the degree of polymorphism, that is, the number of alleles and the frequencies that the alleles are present in the population to be tested. The mere existence of a large number of alleles, e.g., 60, at a particular probe locus in and of itself would not ensure a useful probe if, for example, 99.9% of the population to be tested possessed one allele and the remaining 0.1% was distributed among the other 59 alleles. Thus, the frequency of occurrence of the various alleles is an important consideration.

The number of individual probes in a probe set could be quite large, 100 or more, practical limitations would restrict the number to from 1 to about 40, more preferably from 1 to about 20.

The number of alleles per polymorphoric genetic locus can be large, from 2 to about 60 or more, but more preferably from 2 to about 40. Optimally, the alleles will occur in roughly equally frequency.

Autoradiography

The hybrid is visualized by means of autoradiography. Prior to the hybridization, the probe DNAs are labelled with a radioactive isotope, usually $^{32}P$. The specific activity of approximate $10^8$ counts per min per ug of DNA is required and normally involves labelling with at least two labelled nucleotides (TTP and dCTP 400 Ci/mmol). The radioactive hybridized probe is localized using art recognized procedures involving exposure of film to the radioactive emissions. The radioactive hybrids essentially take their own picture hence the term autoradiography.

Although autoradiography is an art recognized procedure for the localization of the hybrid molecules, the invention is not restricted to this particular mode of analysis. The hybrids of interest may be detected by means of any suitable analytically detectable reagent. For example, fluorescent detection, colorimetric reactions, immunological reactions, or enzymes or other protein-labelled reagents are also useful in the detection of the hybridized probes.

EXAMPLE I

This example illustrates the isolation of DNA from human peripheral blood. DNA so isolated is useful in the evaluation of probe DNA.

Ten to twenty cc. of peripheral blood is collected using EDTA as anticoagulent (Blood may be processed immediately or frozen at 70° C.).

The blood is transferred to a 50 ml tube and an equal volume of lysing buffer (1 mM $MgCl_2$; 1 mM $NaH_2PO_4$, pH 6.5; 0.8% Nonidet P-40; 0.4% deoxycholic acid, sodium salt) is added. The tube is inverted 25–50 times to mix well.

The mixture is transferred to a 50 ml plastic Sorvall tube and spun in an SW 34 rotor at 10,000 rpm (12,000 g) for 30 minutes. The supernatant is discarded and the pellet is suspended in 10 ml of TNE (10 mM Tris, pH 8.3; 150 mM NaCl; 5 mM EDTA). The pellet is disrupted by shaking the tube violently. 1.5 ml of 10% SDS (f.c. 1.0%) is added and inverted several times. Three ml of 5M $NaClO_4$ (f.c. 1.0M) is added and mixed. An equal volume of chloroform: isoamyl alcohol (24:1) is then added and the tube is placed on a New Brunswick gyrotory shaker at 3500 rpm for 15 minutes. The phases are separated by a 10 minute spin at 3,000 rpm in Damon centrifuge.

The aqueous (top) phase is removed with an inverted 10 ml pipette, without cotton (a siliconized Pasteur pipette may also be used) and transferred to a fresh 50 ml tube. The organic (bottom) phase, is discarded, an equal volume of Chl:IAA (24:1) is added and extracted and separated as before. The extraction is repeated until the interphase after phase separation is clear. This usually requires 3–5 extractions.

The aqueous phase from the final extraction is transferred to a plastic beaker. Two to two and one half volumes of −20° C. 95% EtOH is added by slow pouring down the side producing two phases; aqueous-DNA phase on bottom and EtOH on top. A clean, dry glass rod is wound in this solution until the two phases mixed. The DNA precipitates at the aqueous-EtOH interface and is collected on the rod. After the two phases have mixed, the rod is removed and air dried for 10 minutes.

The rod is placed in 15 ml tube and covered with parafilm. Three holes are punched into the parafilm with an 18 gauge needle and the sample is dessicated 20 minutes. The parafilm is removed and 0.5–1.0 ml of 0.01X SSE (1.5 mM NaCl;

0.15 mM EDTA, pH 7.0), is added. The sample is capped and suspended overnight at 4° C. on an Ames rocker.

The amount of DNA in suspension is determined by recording the O.D. of a 1/20 dilution of sample. 25 µl of the DNA suspension is added to 475 µl of distilled water, transferred to a cuvette and the O.D. recorded at 260, 270 and 280 using a cuvette filled with 0.01X SSE to zero each reading. The concentration of DNA in the suspension in mg/ml (µg/µl) equals the reading of a 1/20 dilution at O.D. 260 because the O.D. 260 of 1.000=50 µg/ml. A dilution is made to keep the O.D. 260 between 0.100 and 1.000 where the correlation between DNA concentration and O.D. is linear. O.D. readings above 1.500 are not accurate. The O.D. 260/280 should be 1.8 or greater and measures the amount of protein contamination. For example the following O.D. values were recorded from 0.5 ml of a 1/20 dilution of a DNA suspension form peripheral blood:

| 260 | 270 | 280 | 260/270 | 260/280 | concentration |
|-----|-----|-----|---------|---------|---------------|
| 0.350 | 0.280 | 0.190 | 1.25 | 1.84 | 0.35 µg/µl |

0.350 × 50 µg/ml × 20 = 350 µg/ml = 0.35 µg/µl

EXAMPLE II

This example illustrates a method for the generation of human DNA probes.

A. Messenger RNA Isolation

1. Between $10^7$–$10^8$ human cells are suspended in 2 mls ice-cold Ringer's and centrifuged at 2000X g for 5 minutes at 4° C.

2. Following aspiration of the supernatant, the cells are resuspended in ice-cold lysis buffer. The buffer being comprised of:

0.14M NaCl 1.5 mM $MgCl_2$ 10 mM Tris-Cl pH 8.6

0.5% NP-40

1,000 units/ml RNasin (Biotec)

3. The suspension is vortexed for 10 sec. then underlayed with an equal volume lysis buffer containing sucrose (24% w/v) and 1% NP-40 and stored on ice for 5 minutes.

4. The suspension is centrifuged at 10,000X g for 20 minutes at 4° C. in a swinging-bucket rotor.

5. The turbid; upper (cytoplasmic) layer is recovered and an equal volume of 2X PK buffer is added.

2XPK buffer: 0.2M Tris-Cl pH 7.5

25 mM EDTA 0.3M NaCl

2% S.D.S.

Followed by the addition of proteinase K at a final concentration of 200 µg/ml and incubation at 37° C. for 30 minutes.

6. The layer is then extracted once with phenol/chloroform and the aqueous layer recovered, to which is added 2.5 volumes of ethanol and stored at –20° C. for at least 2 hours.

7. The fraction is centrifuged for 10 minutes at 5000X g at 0° C. and the resulting pellet washed with 75% ethanol containing 0.1M sodium acetate.

8. The nucleic acids are redissolved in a small volume (~50 µl) of:

50 mM Tris-Cl pH 7.5

1 mM EDTA

9. To the resuspended fraction is added $MgCl_2$ to a final concentration of 10 mM and RNasin (Biotec) to 2000 units/mi. The suspension is then incubated for 30 minutes at 37° C.

10. Following incubation, EDTA and SDS are added to a final concentration of 10 mM and 0.2%; respectively.

11. The suspension is extracted with phenol/chloroform and Na acetate pH 5.2 is added to 0.3M and the nucleic acids are precipitated with 2 volumes of ethanol.

12. The RNA in 70% ethanol is stored at –70° C.

B. Selection of poly $A^+$ RNA

1. Oligo (dT)-cellulose is equilibrated in sterile 2X loading buffer. The buffer is composed of 40 mM Tris-Cl pH 7.6.

1.0M NaCl 2 mM EDTA 0.2% SDS

2. The oligo-(dT)-cellulose is used to form a 1 ml column and washed with 3 column volumes each of:

a) sterile water b) 0.1M NaOH/5 mM EDTA c) sterile water

3. The effluent pH should be less than pH 8.0.

4. The column is then washed with 5 volumes of loading buffer.

5. RNA isolated in step A is dissolved in sterile $H_2O$ and heated to 65° C. for 5 minutes. An equal volume of 2X loading buffer is then added and the sample is cooled to room temperature (~25° C.).

6. The sample is then applied to the column and the flow-through is collected. The flow-through is then heated to 65° C., cooled and reapplied to the column.

7. The column is then washed with 5–10 volumes of loading buffer, followed by 4 volumes of loading buffer containing 0.1M NaCl.

8. Fractions are collected and read at $OD_{260}$. Initial fraction will contain poly(A)⁻RNA in high concentration while later fractions will have little or no $OD_{260}$ absorbing material.

9. The poly(A) RNA is eluted from the column with 2–3 volumes of sterile:

10 mM Tris-Cl pH 7.5

1 mM EDTA 0.05% S.D.S.

10. Na Acetate (3M pH 5.2) is added to the eluant to a final concentration of 0.3M and 2.2 volumes ethanol are then added.

11. The RNA is centrifuged at 0° C. at 5000X g for 10 minutes.

12. The pellet is redissolved in water. (10 cells yields 1–5 ug poly(A)⁺ RNA)

C. Synthesis of the First DNA Strand

1. The reaction conditions below assumes a starting amount of 50 µg of polyA⁺ mRNA. For amounts greater or less than 50 g the reaction mixture may be scaled proportionately.

2. Reaction mixture comprising:

| Reagent | Amount to Add | Final Concentration |
|---------|---------------|---------------------|
| 10 mM dATP | 25 µl | 500 µM |
| 10 mM dGTP | 25 µl | 500 µM |
| 10 mM dTTP | 25 µl | 500 µM |
| 2 mM dCTP | 25 µl | 100 µM |
| 5 × Reverse Transcriptase buffer | | |
| 250 mM Tris 8.2; | | 50 mM Tris |
| 250 mM KCl; 30 mM $MgCl_2$ | 100 µl | 50 mM KCl; 6 mM $MgCl_2$ |

| Reagent | Amount to Add | Final Concentration |
| --- | --- | --- |
| 200 mM DTT | 25 µl | 10 mM |
| Poly(A) mRNA | (50 µg) | |
| RNasin (Biotec) placental RNase inhibitor | 5 µl | |
| Avian myleoblastosis virus reverse transcriptase | 20 µl | 300 µ/ml |
| Oligo(dT) 12–18 600 ug/ml | 37.5 µl | 45 µg/ml |
| $^{32}$P-dCTP | 1–10 uCi/500 µl reaction | |
| distilled H$_2$0 | To final volume: 500 µl | |

3. The reaction is performed in a 1.5 ml siliconized Eppendorf tube and initiated by the addition of the mRNA.

4. The reaction mixture is incubated at 42° C. for 60 minutes, then 10 ul of 500 mM EDTA is added to stop the reaction.

5. 1 µl of the reaction mix is precipitated with T.C.A. and counted to determine the efficiency of 1st stranded synthesis. Generally, 17–25% efficiency is obtained, rarely as high as 40%.

6. 10 µ Ci of $^{32}$P-dCTP/500 ul will yield a specific activity of $2.2 \times 10^6$ cpm/µg of single stranded DNA. The specific activity allows maintaining of the product in subsequent step without wasting too much of the cDNA.

7. The sample is extracted twice with an equal volume of phenol saturated with 50 mM Tris pH 8.0.

8. The phenol is extracted twice with volumes of ether. After which is added 3M Na acetate to 0.3M.

9. Three volumes of 95% ethanol are added and the mixture is placed on dry ice-ethanol for 5–10 minutes then warmed to room temperature.

10. The mixture is spun in a microfuge for 15 minutes after which time the supernatant is discarded and the pellet washed with 75% ethanol.

11. The DNA is redissolved in 0.5 ml of 300 mM Na acetate and steps 9 and 10 are repeated.

12. The DNA is resuspended in 200 µl of distilled water, layered on 5–20% alkaline sucrose gradient (30 mM NaOH, 2 mM EDTA) and spun for 40 minutes in an SW-40 rotor at 37,000 rpm at 4° C.

13. 0.5 ml fractions are collected from the top of the gradient and place into 25 µl M Tris pH 6.8 and each fraction counted.

14. Five thousand-ten thousand counts per minute from every other fraction are removed and run on an alkaline agarose gel. This permits a size distribution estimate to be made. Generally fractions which have cDNA of less than 500 nucleotides are discarded. Fractions particularly useful (i.e., at least 500 nulceotides long) usually occur at fraction 12 from the bottom of the tube. Therefore while the gel is running and developing, fractions 1–10 (including the pellet) are pooled and dialyzed against 2 liters of water fractions 11, 12, 13 and 14 are also dialyzed but individually. The gel pattern will indicate whether or not further pooling is necessary. In general material greater than 500 nucleotides will account for 60% of the TCA-precipitable counts.

15. The ss cDNA is then concentrated with sec-butanol to a volume of ~400 µl followed by extraction of the butanol with ether.

16. To the extract is added 40 ul 3M Na acetate and the remainder of the tube is filled with 95% ethanol. Precipitate on ethanol-dry ice for 5 minutes then place the tube in a water filled bucket of SW-27 rotor and centrifuge at 25,000 rpm for 60 minutes.

17. The ethanol is decanted and counted. The ethanol should contain less than 1% of the counts. Wash the pellet with ethanol and count the wash solution again; less then 1% of the counts should be removed. All counts should remain in the pellet which is lyphilized for 10–20 minutes and then resuspended in 100 µl of water.

D. Second Strand Synthesis With Klenow

1. The reaction mix below is for a 1 ml reaction at a concentration of ss cDNA of 2–5 µg/ml.

| Reagent | Amount to Add | Final Concentration |
| --- | --- | --- |
| 10 mM dATP, TTP, CTP, GTP | 50 µl | 500 µM |
| 700 mM KCl | 100 µl | 70 mM |
| 5 mM mercaptoethanol (Add 1.8 ul of stock Eastman (14 M) to 5 ml H$_2$O to yield 5 mM) | 100 µl | 0.5 mM |
| 10 × Klenow buffer 300 mM Tris pH 7.5 40 mM MgCl$_2$ | 100 µl | 30 mM Tris 4 mM MgCl$_2$ |
| Klenow polymerase Boehringer-Mannheim | | 150–200 units/ml |
| SS c DNA | 2.5 µg | |
| distilled H$_2$O | To final volume of 1000 µl | |

2. The reaction is incubated at 18°–20° C. for 5–6 hours.

3. The mixture is extracted twice with phenol-Tris pH 8 and ether.

4. An aliquot (2–10,000 cpm) is saved for gel analysis.

5. The remaining extract is dialyzed over night against water in a colloidon bag.

E. S1 Reaction

1. The volume of the Klenow reaction of step D will increase to 5–6 ml during dialysis. The volume is adjusted to the next highest ml with d H$_2$O and one-tenth volume of 10×S1 buffer is added:

3M NaCl 0.3M Na Acetate pH 4.5

100 mM ZnCl$_2$

2. S1 nuclease (Sigma) is added to a final concentration of 10 units/ml and incubated at 37° C. for 30 minutes and stop the reaction by the addition of 500 mM EDTA to a final concentration of 100 mM. An aliquot is saved for gel analysis.

3. The reaction mix is extracted twice with phenol and twice with ether. The extract is then dialyzed for 5–6 hours at room temperature vs water with at least one change of water and then concentrated with sec-butanol to ~400 µl.

4. The sample is loaded onto a neutral 5–20% sucrose gradient (0.1M NaCl, 10 mM Tris, pH 7.5, 1 mM EDTA) and centrifuged at 37,000 rpm is SW-40 rotor for 20 hours at 4° C.

5. Fractions of 0.5 ml are collected from the top of the tube. Fractions 1–14 will contain ~500 bps of ds cDNA. Gels are run to verify the size distribution.

6. The fractions are dialyzed exhaustively overnight against distilled water.

7. The sample is concentrated to ~400 µl with sec-butanol and precipitated with Na acetate and ethanol twice. The pellet is washed each time with 75% ethanol. The DNA must be contaminant free.

8. The ds cDNA is then lyophilized.

F. Tailing Reaction

1. The reaction conditions below are for 1 µg ds cDNA and may be scaled up or down accordingly.

Stock solutions: 50 µM dCTP 10 mM CoCl$_2$ 2X cacodylate buffer: 250 µl 1.2M Na-cacodylate, pH 7.19 with HCl 250 µl mM DDT 750 µl H$_2$O

| Reagent | Amount to add |
| --- | --- |
| 2X cacodylate buffer | 200 µl |
| cDNA (50 ng/ul) | 20 µl (1 ug) |
| 50 µM dCTP | 40 µl |
| 20 µM CoCl$_2$* | 20 µl |
| 25 mg/ml BRL nuclease free BSA | 8 µl |
| dH$_2$O | 68 µl |
| TdT (Bethesda Res. Lab) | 44 µl (760 u/ml final conc) |

*Add CoCl$_2$ just before BSA or it will precipitate.

2. The reaction mixture (-TdT) is incubated at 20° C. for 20 minutes.

3. The TdT is then added and the incubation continued for another 20 minutes.

4. The reaction is stopped by the addition of 8 µl of 500 mM EDTA and then extracted twice each with phenol then ether.

5. The sample is precipitated as above with sodium acetate, ethanol in the SW-27 rotor.

6. The pellet is washed with 7.5% ethanol, lyophilized and resuspended in 50 µl of distilled water.

G. Annealing Tailed cDNA to plasmid-dG

1. The annealing reaction is performed in 10 µl sealed capillary tubes.

2. The reaction mix comprised:

ds cDNA 1 µl (5 ng)

plasmid 1 µl (20 ng)

10X annealing buffer

1M NaCl 100 mM Tris; pH 7.5

10 mM EDTA distilled H$_2$O 7 µl

3. The mixture is incubated at 68° for 8 minutes, then at 42° C. for 2 hours after which time the water bath is turned off and the reaction mix allowed to equilibrate to room temperature (5 hours—overnight).

EXAMPLE III

This example illustrates the methods of identification of probes which are useful in the detection of polymorphisms in humans.

1. DNA is isolated from the peripheral blood of 4 different human subjects as described in Example I.

2. The four samples of DNA are restricted separately with restriction enzyme EcoRI according to the following procedure.

a) The following components are added to a 1.5 ml eppendorf tube:

(1) Enough of the DNA solution for 10 µg (usually between '10 µl and 50 µl).

(2) Distilled water, if necessary, to adjust to the final reaction volume.

(3) The appropriate amount of the specific 5X endonuclease digestion buffer made to the manufacturer's recommendations.

(4) Restriction endonuclease in 1.5 to 2.5 fold excess, i.e., 15 units to 25 units for a 10 µg digestion.

b) The mixture is vortexed 1–2 seconds or the tube is flicked with a finger several times to mix.

c) The mixture is spun in eppendorf microcentrifuge 10–15 seconds to pellet reactants.

d) The pellet is incubated 2–16 hours at 37° C.

e) The reaction is stopped to store for future electrophoresis adding:

(1) 1/10 volume of 0.1M EDTA, pH 7.0; f.c. 10 mM (2) 1/10 volume of 5% SLS; f.c. 0.5%.

(3) 1/10 volume of 3M NaCl or 3M NaAcetate; f.c. 0.3M (4) 2 to 2½ volumes of cold 95% EtOH; f.c. about 70%

The sample may be stored to −20° C. for up to several months.

Samples can be precipitated quickly by placing an eppendorf tube containing the digested DNA, stop reactants, and EtOH in a dry ice-EtOH bath for 2–5 minutes depending on the volume until the EtOH is viscous. The samples should not be frozen. The sample is spun in microfuge to pellet.

f) To stop reaction which is to be loaded to gel immediately after digestion, add 5X ficoll marker dye solution to a final concentration of 1X. This is done with samples where the final volumes is less than 75 µl.

g) A typical reaction mixture is constructed as follows:

| 10 mgDNA | H$_2$O | 5x buffer | EcoRI 5 µ/µl | 0.1 M EDTA | 5% SDS | 3 M NaCl | 95% EtOH |
| --- | --- | --- | --- | --- | --- | --- | --- |
| 20 µl | 16 µl | 10 µl | 4 µl | 6.25 µl | 6.25 µl | 7.0 µl | 14.0 µl | and incubated at 37° C. for 2 hours. The EDTA, SDS, NaCl, and EtOH are added as indicated and store at −20° C. or add 12.5 µl of 5X Ficoll marker dye and load on gel.

3. The DNAs are subjected to electrophoresis as described in Example II running 5 µg of each of three of the individuals DNAs in one lane and 5 µg of DNA from the fourth individual in an adjacent lane.

4. The electrophoresed DNAs are then blotted according to the following procedure:

a) The DNA is denatured in the gel by transferring the gel to a blotting bowl (round pyrex, 190×100 mm) containing 250 ml of 1M KOH, 0.5M NaCl and shaken at 200 rpm at room temperature on a New Brunswick gyrotory shaker 25 minutes for an 0.8% gel to 30 minutes for a 1.2% gel.

b) Precut nitrocellulose sheets (9½×15 cm) are placed in 200–300 ml of distilled water to thoroughly wet.

c) The solution is decanted and saved (KOH—NaCl solution may be used to denature up to 10 gels.) The gel is rinsed with distilled water (200–300 ml). All rinsed water is removed with Pasteur pipette. 250–300 ml of 1M Tris, pH 7.0 is added and shakeing is continued at room temperature at 50 rpm for 35 minutes.

d) The gel is neutralized by decanting and add 250–300 ml of 1M Tris, pH 7.0 and continuing to shake for 30 minutes. The Tris solutions are saved and adjusted back to pH 7.0 with concentrated HCl up to 10 times.

e) Optionally, the gel is decanted, 250–300 ml of 1M Tris, pH 7.0 is added and shaking is continued for 25 minutes.

f) All of the Tris is decanted and removed with a Pasteur pipette. The gel is equilibrated by adding 250–300 ml of 6SSC (1X=0.15M NaCl, 0.015M NaCitrate) and shaken for 20 minutes.

g) The distilled water is decanted from the nitrocellulose and 100–200 ml of 6X SSC is added.

h) Using a pyrex 28×18×4 cm tray add 600–700 ml of 6X SSC. A wick of two strips of Whatman 3 M (15½×38 cm) is wetted in the 6X SSC solution. A plastic blotting platform (18½×19×1 cm) is placed in the middle of the tray and the Whatman 3 M wick is centered on the platform so that each end is submerged in the 6X SSC solution.

i) While wearing gloves, the gel is transferred from the bowl to the wick. The gel is rubbed with gloved fingers to ensure contact with gel and wick.

j) The presoaked nitrocellulose (Schleicher and Schuell, Keene, N.H.) is placed on the gel and positioned over the lanes to be blotted. Rubbing with gloved fingers ensures contact of the gel and nitrocellulose and the appearance of no air bubbles. The gel not to be blotted is trimmed and discarded. Three pieces of a 1 ml pipette are placed along each side of the gel to avoid short circuits. One piece of Whatman 3 M (15½×9½) is wetted and placed on top of nitrocellulose. Another similar sized dry piece of Whatman 3 M is added. About 10 cm of 10½×12 cm brown towels (No. 237 Singlefold Garland Sof-knit Towels; Fort Howard Paper Company, Green Bay, Wis. 54305) are stacked on top of gel. Cover by plastic wrap pulling tight around tray. The apparatus is left for 12–20 hours at room temperature. The blotting platform is placed on top for weight.

k) The towels are removed (some of the top ones may still be dry) along with two pieces of Whatman 3 M exposing nitrocellulsoe paper. A new razor blade is used to cut the nitrocellulose sheet into three strips containing 2 or 3 lanes worth of DNA (2 lanes each with the 8-lane well former and 3 lanes each with the 10-lane well former). The lower left corner of each strip is nicked for orientation and one, two or three holes are punched into the bottom of the appropriate strips for identification. After the strips have dried, they can be labelled with a marking pen.

l) The strips are placed in 250 ml of 2X SSC in a blotting tray. Each side of the strips are rubbed with gloved fingers to remove bits of aragose. The strips are placed on Whatman No. 1 filter paper to air dry for 10–20 minutes. The strips are then placed between two pieces of Whatman 3 M paper and wrapped in aluminum foil. The outside is labeled with marking pen and may be placed in vacuum in dessicator for up to 6 months.

5. *E. coli* MC1061 carrying recombinant plasmids are cultured in 100 ml L broth from an individual colony of the library generated in Example II and plasmid DNA is isolated according to the following procedure:

a) The cells are centrifuged at 5000 rpm for 5 minutes at 0° C.

b) The cells are washed with ¼ volume of TE (10 mM Tris-HCl, 1 m EDTA pH8) at 0° C.

c) The cells are resuspended in 3 ml of 25% sucrose, 0.05M Tris HCl pH 7.5 at 0° C. and 0.3 ml lysozyme (10 mg/ml in 0.25M Tris-HCl pH 7.5) is added; followed by incubation on ice for 5 minutes with occasional gentle swirling.

d) 1.2 ml of 250 mM EDTA pH8 is added and incubation on ice is continued for 5 minutes.

e) 48 ml of Triton solution:

2 ml 10% Triton X 100 (Sigma)

50 ml 250 mM EDTA pH:

135 ml $H_2O$ is added and incubated on ice for an additional 10 minutes.

f) The mixture is spun for 30 minutes at 25,000 rpm at 0° C.

g) The supernatant is removed and the volume is adjusted to 8.7 ml followed by the addition of 8.3 g of CsCl and 0.9 ml of 10 mg/ml ethidium bromide (Sigma #E-8151). The refractive index should be between 1.390 and 1.396.

h) The sample is centrifuged at 35–38K at 20° C. for 48–72 hours and visualize the bands by illuminating the tube with long wavelength ultraviolet light.

i) The lower band which contains the supercoiled DNA is collected by side puncture of the tube with a 21 guage needle.

6. The pAT 153-human DNA recombinants are labelled with $^{32}p$ by nick translation as is well known in the art ("A Manual for Genetic Engineering. Advanced Bacterial Genetics" by Davis, R. W., Botstein, D. and Roth, J. R. 1980 Cold Spring Harbor Laboratory, Cold Spring Harbor, N.Y., pp. 168–170).

a) 20 µl of water minus the volume of the DNA solution which is to be added is placed in a microfuge tube.

b) 2.5 µl of 0.5M Tris pH 7.5, 0.1M $MgSO_4$, 10 mM pTT, 500 µg/ml BSA is then added.

c) 2.5 ul of a solution containing 0.2 mM each dNTP followed by the addition of 100 mg of pAT 153 human recombinant DNA from step 5 above.

d) A DNase stock solution:

DNase 1 mg/ml in 50 mM Tris pH 7.5

10 mM $MgSO_4$ 1 mM DTT and 50% glycerol is previously prepared and stored at –0° C.

e) The DNase stock solution from (d) above is diluted at 0° C. 1/40,000 into 50 mM Tris pH 7.5, 10 mM $MgSO_4$ 1 mM DTT and 50 µg/ml BSA and 0.5 ul of the diluted DNase is added to the reaction mixture.

f) 10 µCi of each $^{32}P$ dNTP in aqueous solution is added.

g) The entire reaction is initiated by the addition of 0.1 µl of 2 mg/gl *E. coli* DNA polymerase I and incubated at 14° C. for 3 hours.

h) 25 µl of 0.02M $Na_3$ EDTA 2 mg/ml carrier DNA, and 0.2% SDS is added to stop the reaction.

i) The reaction mixture is loaded onto a 0.7×20 cm Sephadex G-50 (medium) column preequilibrated with 10 mM Tris $Na_3$ EDTA at pH 7.5 (TE) and washed with same.

j) 0.5 ml effluent samples are collected in polypropylene tubes. The DNA appearing after 2 ml of wash. The location of the $^{32}P$-labelled DNA is followed with a hand-monitor and the first peak is collected ignoring the tail.

7. The labelled probe from step 6 is hybridized to the blotted genomic DNAs from step 4 according to the following procedure:

a) 300 ml of prehybridization solution is prepared as follows:

1) 100 ml 3X $PO_4$ (0.75M $Na_2PO_4$, 0.75M $NaH_2PO_4$, 0.01M NaPyrophosphate)

2) 90 ml 20X SSC (3M NaCl, 0.3M NaCitrate)

3) 92 ml distilled water 4) 15 ml 0.5% BFP (0.5 g per 100 ml each of; bovine serum albumin, ficoll, and polyvinylpyrolidone-360)

5) 3 ml 5 µg/µl ssDNA (denatured salmon sperm DNA). The solution is transferred to plastic bin with top (20×14½× 10½ cm) and heat to 68° C. in water bath. The filters to be hybridized are added and incubated for 4 to 6 hours at 68° C.

b) For hybridization strips, 3 to 4 strips are wrapped around a siliconized glass vial and inserted into a plastic scintillation vial containing 2 ml of hybridization solution. For hybridization of nitrocellulose sheets in bags, the appropriate amount of hybridization solution is added and the bag sealed with heat from a Sears seal-it device.

The hybridization solution is made as follows for hybridization in a vial:

(1) 80 µl 0.5% BFP
(2) 20 µl 0.1M EDTA, pH 7.0
(3) 20 µl 10% SDS
(4) 20 µl 5 µg/µl ssDNA
(5) variable $^{32}$P nick translated probe to give 2–4×10$^6$ counts/ml
(6) variable distilled water to adjust to 1900 µl boil 12 minutes; ice 7 minutes (7) $\dfrac{100 \ \mu l}{2000 \ \mu l}$ 20 × SSC c) Wearing gloves, the strips are removed directly from the prehybridization solution and the appropriate 3 or 4 strips are wrapped around a siliconized glass vial (19×48 mm with cap) and inserted into a plastic scintillation vial (28 mm diameter) containing the prepared hybridization solution.

Parafilm is wrapped around the canned lid. Tapping several times ensures the filters are all at the bottom of vial. The filters are incubated 20–24 hours at 68° C. in a New Brunswick gyratory water bath with slow shaking (setting number 3). Note: If there are less than 3 strips to wrap around the vial, one or two blank strips which have been prehybridized can be added.

d) The filters are washed in 2X SSC, 0.5% SDS as follows: 6–9 liters of wash solution is prepared depending on the number of filters to be washed. To a glass carboy with stopcock at the bottom is added:

(1) 600 to 900 ml 20X SSC
(2) 300 to 450 ml 10% SDS
(3) 5100 to 7650 ml distilled water A stir bar is placed at the bottom and a thermometer is suspended from the top. The solution is heated to 68° C. on hot plate with stirring.

1 to 1½ liters of wash solution is collected in plastic bin. The filters are removed after hybridization (wearing gloves) and immersed immediately in wash solution. Millipore forceps are used to unroll and transfer filters.

e) The filters are transferred to 1 to 1½ liters of fresh wash solution and incubate 7–12 minutes at 68° C. in water bath. The first wash solution is carefully discarded down the drain with plenty of water to flush.

f) The filters are again transferred to 1 to 1½ liters of fresh wash solution. Continue to transfer every 7–12 minutes and incubate at 68° C. until all of the wash solution is used (4–7 washes).

g) The final transfer is to 1 liter of wash solution containing 0.1X SSC, 0.5% SDS (945 ml distilled water, 50 ml 10% SDS, 5 ml 20X SSC) heated to 68° C. Incubation is at 68° C. for 10 minutes.

h) The filters are removed and rinsed in 500 ml of 2X SSC at room temperature. Filters are placed on sheet of Whatman No. 1 to air dry 15–30 minutes.

i) The 6 strips from two gels are taped on yellow paper from an x-ray film pack, labeled, covered with plastic wrap and placed in cassette with built in intensifying screens. In dark room, the cassette is loaded with 8×10 inch X-Omat AR x-ray film placing film between nitrocellulose strips and screen. The cassette is closed and placed in a freezer at −70° C.

j) The x-ray film is developed in 24 to 48 hours. The film is removed from cassette and developed in dark room with yellow safe light on. The cassette may be reloaded if another exposure is required.

8. If the tested probe yields more bands in the lane with three individuals' DNAs than in the lane with only one individual's DNA it becomes a candidate to detect polymorphisms.

9. Probes identified in step 8 are further tested by hybridizing them against a larger series of human DNAs to determine the extent to which the cloned region is polymorphic. Probes corresponding to regions with at least four different alleles present in the population with frequencies greater than 10% each are incorporated into the test for paternity or the test for individual identity.

EXAMPLE IV

This illustrates the performance and evaluation of a paternity test employing the subject invention.

1. Blood samples are taken from the mother, child, and putative father and DNA purified as described in Example I.

2. These DNAs separately reacted with restriction enzyme EcoR1 as described in Example III.

3. These DNAs are subjected to electrophoresis as described in Example II running 5 µg of each of the mother's and the putative father's DNAs in one lane and 5 µg of DNA from each of the three individuals in an adjacent lane.

4. The electrophoresed DNAs are blotted as described in Example III.

5. The set of "paternity probe" DNAs is labelled with $^{32}$P as described in Example III.

6. The labelled probe DNAs from step 5 are hybridized with the blotted genomic DNAs from step 4 as described in Example III.

All genes of the child will be derived from either the mother or father. Therefore, if the putative father is the biologic father all bands present in the lane with the child's DNA will also be present in the lane without the child's DNA. Conversely, if the putative father is not the biologic father, new bands will appear in the lane with the child's DNA.

EXAMPLE V

This example provides specific techniques for and evaluation of a paternity test.

A. DNA PURIFICATION FROM BLOOD

1. Samples of blood (5 to 10 ml) should be collected in tubes containing EDTA or Citrate as anticoagulant and stored at 4° C. until processed.

2. Resuspend cells by inversion and centrifuge at 2,000 rpm for 10 minutes at 4° C. Remove serum (top) without disturbing buffy coat.

3. Add equal volume of blood lysis buffer (0.32 sucrose, 10 mM Tris pH 7.6, 5 mM MgCl, 1% Triton X-100) at 4° C. and mix well by inversion. Transfer into a 50 ml polypropylene conical tube (e.g. Corning, Falcon), rinse blood tube and adjust final volume to 4 times the original blood volume. Mix well and centrifuge at 2,000 rpm for 10 min. at 4° C.

4. Decant supernatant. If pellet is not clean (i.e. too much red cell contamination), then resuspend pellet in 3 ml of lysis buffer and centrifuge again.

5. Resuspend whitish-pink pellet in 2.5 to 5 ml of DNA lysis buffer (10 mM Tris pH 7.4, 10 mM EDTA, 10 mM NaCl, 100 µg/ml of Proteinase K). Mix well and vortex if necessary. Add SDS (stock solution: 20%) to 1% final concentration. Mix by gently inverting the tube. The sample will turn very viscous. Place in rocker platform at 37° C. overnight with gentle mixing or at 60° C. for 3 hours with occasional mixing.

6. Add NaC104 to 1M final concentration from a 6M stock (i.e. dilute 1:5). Mix gently by hand or in rocker platform. At this point, the sample can be stored in the cold indefinitely.

7. Add equal volume of phenol-chloroform mix (1 part 90% phenol, 10% 1M Tris pH 8.0:1 part $CHCl_3$) and gently shake (e.g. wrist shaker) for 15 to 30 minutes at room temperature.

8. Transfer to 15 ml glass Corex tube and centrifuge at 4,000 rpm for 15 min. (beckman) or 10,000 rpm for 5 min. (Sorvall) to separate the phases.

9. Remove top aqueous phase with wide mouth pipete and return to original plastic tube. Repeat this extraction procedure 2 more times.

10. Place DNA sample into an appropriately marked dialysis bag and dialyze against 100 fold excess of TE buffer (10 mM Tris pH 7.4, 1 mM.

11. Read O.D. of an appropriate sample dilution (e.g. 1/20) against same type of blank solution at:

240 nm (for EDTA); 250 nm (max. for DNA); 270 nm (max for phenol); 280 nm (max. for proteins); 340 nm (turbidity). 260/270: approx. 1.2; 260/280:approx. 1.8.

B. RESTRICTION ENDONUCLEASE DIGESTION OF GENOMIC DNA:

1. Add the following components to a 1.5 ml eppendorf tube:
    a) Take approximately 10 µg of DNA/test (usually between 10 µl and 50 µl).
    b) The appropriate amount of the specific 10X endonuclease digestion buffer made to the manufacturer's recommendations.
    c) Restriction endonuclease in 3 fold excess.

2. Vortex 1–2 seconds or flick tube with finger several times to mix.

3. Spin in eppendorf microcentrifuge 10–15 seconds to pellet reactants.

4. Incubate 2 hours at 37° C. for EcoR1 or 65° C. for Taq I.

5. a) Add 1/10 volume of 3M $NH_4$ Acetate.
   b) 2 to 2½ volumes of cold 95% EtOH.
   c) Store at –20° C. overnight. Spin in microfuge to pellet (15 minutes at 4° C.).

6. a) Dissolve pellet in 15 of $H_2O$.
   b) Add the appropriate 10 X of restriction enzyme buffer and a 3 fold excess of restriction endonuclease and repeat steps 2, 3, and 4.

7. To stop reaction which is to be loaded to gel immediately after digestion, add 5X ficoll marker dye solution to a final concentration of 1X. This can be done with samples where the final volume is less than 20 µl.

C. ELECTROPHORESIS

1. Prepare agarose gel by boiling agarose in 1X TAN (40 mM Tris, pH 7.9; 4 mM NaAcetate, 1 mM EDTA). Final concentration of agarose should be between 0.4% and 1.2% depending on the size of the fragment to be fractionated. Samples to be hybridized to pAW-101 are electrophoresed in 0.4% agarose, while for hybridization to pLM 0.8 use 1.2% agarose.

2. When agarose solution reaches about 75° C., add EtBr (2,7-diamino-10-ethyl-9-phenyl-phenanthridinium bromide) to a final concentration from 500 ng/ml to 12.5 ng/ml.

3. Immediately pour into a horizontal gel electrophoresis mold to produce a gel approximately 4 mm thick. Place a well former at one end of mold. Allow to cool at room temperature until solid. Remove well former and cover gel with 1X TAN.

D. Layer the samples into the gel wells. Connect the gel box to the power supply. Turn on the power supply and dial up the current to the appropriate value. For example, to separate fragments of over 10 kb, electrophorese at 20 V for 3 days. For 1.5 kb fragments, electrophorese at 40 V overnight (16–20 hours) and after electrophoresis, disconnect the tank. Wearing gloves, remove gel with gel scoop. Place gel on u.v. light box and lay a clear ruler along side the lane with marker DNA. Take a picture of the gel with an appropriate photographic film to keep as a record of the electrophoresis.

D. PLASMID QUICK PREP 1. 15 ml of *E. coli* HB101 carrying either pAW101 or pLMO.8.

2. Centrifuge 10 min. at 8,000 rpm.

3. Pellet vortexed.

4. Add 300 of 25% sucrose; 50 mM Tris pH 8.0; 0.1 EDTA; 0.2 mg/ml RNase; 1 mg/ml Lysozyme.

5. Leave in ice for 15 min.

6. Add 250 0.5% Triton X-100; 50 mM EDTA; 50 mM Tris pH 8.0.

7. Leave for 5 min. on ice.

8. Spin at 4° C. for 30 min. 25K in SW-25, 27 or 41.

9. Separate pellet from supernatant. (Pellet is a gelation of bacterial DNA).

10. To the supernatant, add 10 of Proteinase K (5 mg/ml).

11. Leave 5 min. at R.T.

12. Extract once with 1:1=phenol: $CHCl_3$; twice with $CHCl_3$.

13. Aqueous phase add NH 4 Acetate to 0.3M final concentrate.

14. Add 2.5 X vol. ethanol.

15. Leave in freezer (–20° C.) overnight.

16. Centrifuge, dissolve the precipitate in 20 mM Tris pH 7.4, 10 mM EDTA.

17. Add CsCl for banding.

E. NICK TRANSLATION

1. For each hybirdization reaction mix:
    a) 50 nanograms of native probe DNA.
    b) 0.7 µl of 10X nick translation buffer (1X=25 mM Tris. HCl pH 7.9, 2.5 mM MgCl, 5 mM DTT, 100 µg/ml of bovine serum albumin).
    c) 2.5 µl of alfa P-32 deoxynucleotides triphosphate (25 µCi).
    d) 0.5 µl of DNAse I at 20 picograms/µl.
    e) 0.5 µl of DNA polymerase I (3 units).
    Final volume is adjusted to 5 µl.

2. Incubate at 16° C. for 2 hours.

3. Stop reaction by adding EDTA to a final concentration of 10 mM and SDS to 0.5% final concentration. Final volume 100 µl.

4. Separate labeled DNA from unreacted triphosphates by centrifugation of reaction mixture through 0.6 ml of SEpharose 6B-CL in a pierced microcentrifuge tube at 1500 rpm for 2 min.

5. Take 1 µl of the flow through material (i.e. containing the labeled DNA, and count in a beta scintillation spectrometer.

F. SOUTHERN TRANSFER PROTOCOL FOR ZETA-MIND

1. Run DNA on agarose gel. Stain with ethidium bromide (10 µg/ml) for 15 to 30 min., remove excess stain by soaking buffer for 15 to 30 min. and photograph.

2. Soak gel in 0.5M NaOH, 1.0M NaCl for 30 min. with gentle agitation.

3. Rinse gel with water and repeat step 2 with 0.5M Tris. HCl pH 7.5, 0.3M NaCl.

4. Wet Zetabind with water. Then soak for 30 min. in Na phosphate buffer (0.025M pH 6.5).

5. Soak gel for 15 min. in the same phosphate buffer of step 4 for 20 min.

6. Place two strips of WHatman 3 MM wet in phosphate buffer, the size of gel. Make sure that there are no air bubbles trapped in between. Place gel (filters down) over tray with a 3 MM paper wick submerged in phosphate buffer. Place Zetabind on the gel, then two 3 MM paper strips and finally paper towel (3–4 inches high). Place a flat tray on top and some weight (e.g. a 100 ml bottle) to ensure uniform contact between gel and papers.

7. Transfer overnight using phosphate buffer (0.025 m pH 6.5).

8. Wash membrane with phosphate buffer for 15 min. (rub gently the side of the membrane that was in contact with gel).

9. Bake in vacuum oven for 2 hours at 80° C.

10. Place in Seal-a-meal bag and wash for 30 to 60 min. at 60° C. in 0.1 X SCC, 0.5% SLS (approx. 15 ml).

11. Pour off buffer from step 10 and replace with prehybridization buffer (4 X SSC, 50 mM Na phosphate pH 6.7, 5 X Denhardt, 200 ug/ml of denatured salmon sperm DNA and 50% formamide). Incubate 3 to 16 hours at 37° C.

12. Denature the probe by heating in 1 ml of hybridization buffer for 10 min. at 70° C. Hybridize with the denatured radioactive DNA for 40 to 72 hours at 37° C($2\times10$ dpm/bag).

13. Wash with 2 X SSCP, 0.1% SLS at 65° C. agitating for 20 min. until a 10 ml aliquot of the wash has less than 100 cpm Cherenkov (approx. 6 times). Wash twice with 0.4 X SSCP, 0.02% SLS at 65° C. and twice with 0.1 X SSCP. Each time add enough buffer to cover filters.

14. Blot Zetabind and let air dry before covering with cellophane and placing in the cassette for autoradiography.

Before reusing, remove probe by heating at 70° C. for 10 min. in prehybridization buffer.

PREHYBRIDIZATION (for 15 ml total volume)

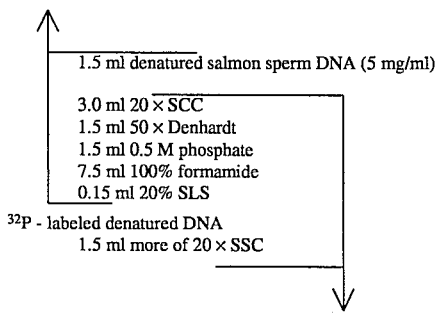

HYBRIDIZATION (for 15 ml total volume).

15. The 6 strips from two gels are taped on yellow paper from an x-ray film pack, labeled, covered with plastic wrap and placed in cassette with built in intensifying screens. In dark room, the cassette is loaded with 8×10 inch X-omat AR x-ray film placing film between nitrocellulose strips and screen. The cassette is closed and placed in a freezer at –70° C.

16. The x-ray is developed in 24 to 48 hours. The film is removed from cassette and deeloped in dark room with yellow safe light on. The cassette may be reloaded if another exposure is required.

EXAMPLE VI

This Example illustrates the specific performance and evaluation of a paternity test employing the subject invention.

1. Blood samples are taken from the mother, child and putative father and DNA purified as described in Example V A.

2. These DNAs are separately reacted with either restriction enzyme EcoR1 or Taq 1 as described in Example V B.

3. These DNAs are subjected to electrophoresis as described in Example V C using 5 μg of one of the three DNAs in each of three adjacent lanes in order (from left to right) mother, child putative father.

4. "Paternity Probe" DNA's are prepared and labelled as described in Examples V D and V E.

5. The electrophoreses DNAs are blotted as described in Example V F.

6. The labelled probe DNAs from step 4 are hybridized with the blotted genomic DNAs from step 5 as described in Example V E. pAW 101 DNA is hybridized to EcoR1 cut genomic DNA while pLM 0.8 is hybridized to Taq 1 cut genomic DNA.

7. Autoradiograms are made as described in Example V F.

8. Following autoradiography, the size of the bands corresponding to the polymorphic DNA fragments are determined. This accomplished by measuring the distance migrated by these bands, relative to that of a collection of DNA molecular weight standards (Southern, E. M., [1984] Anal. Biochem. 100, 319–323).

The size of the DNA fragments, in each of the individuals of a family, are compared and used to determine whether the pattern observed in the child is consistent with those measured in the putative father. If the size of the DNA fragments i the child are different to that of the presumptive father, then it is concluded that he is not the biological father (i.e. case of non-paternity). If the child shares only one allele with the mother then it can be concluded that the other allele was inherited form the father. If the putative father does not possess this allele it can be concluded that he is not the father. Alternatively, if the two share at least a pair of DNA fragments, not contributed by the mother than the determination of whether or not that individual might be the father is based on the probability that a random individual from the population might have that same DNA fragment size (i.e. paternity index; in Inclusion Probabilities in Parentage Testing [1983], ed. R. H. Walker, American Association of Blood Banks). In this latter case it is necessary to know the frequency of the alleles detected with the particular DNA probe. The observed frequencies for the probes pAW-101 and pLM-0.8 are given in tables 1 and 2.

EXAMPLE VII

Test Case 1

Using the procedures of Example VI a mother, child and putative father were tested using the subject invention. FIG. 1 shows a picture of the autoradiogram obtained using pAW101 as a probe against EcoR1 cut DNA obtained format he mother, child and father. Measurement of migration distances and comparison with known standards indicated that the mother carries pAW101-alleles number 2 and 5, the child carries pAW101-alleles number 5 and 10 while the putative father carries pAW101-alleles numbers 10 and 11. Since the mother must have contributed pAW101-allele number 5 to the child the father must have contributed allele number 10. One now can compare the chance that the putative father would contribute pAW101 allele number 10 to a child vs the chance that a random man would contribute allele number 10. In this case, the likelihood ratio if 16.67 which translates into a chance of paternity of 94%.

EXAMPLE VIII

Test Case 2

Figure 2:
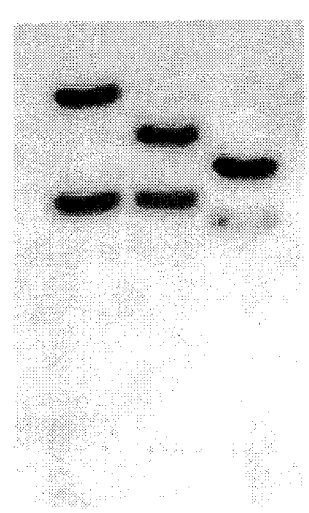
FIG. 2 represents the autoradiograph as described in Example VIII.

Using the procedures of Example VI, a mother, child and putative father were tested using the subject invention. FIG. 2 shows a picture of the autoradiogram obtained using pAW101 as a probe against EcoR1 cut DNA obtained from the mother, child and father. Measurement of migration distance and comparison with known standards indicated that the mother carries pAW101-alleles number 5 and 9, the child carries pAW101-alleles numbers 5 and 7 while the putative father carries pAW101-alleles number 4 and 6. Since the father of this child must have contributed allele 7 to the child and the putative father does not carry this allele, he is excluded as a possible father.

EXAMPLE IX

Test Case 3

Figure 3:
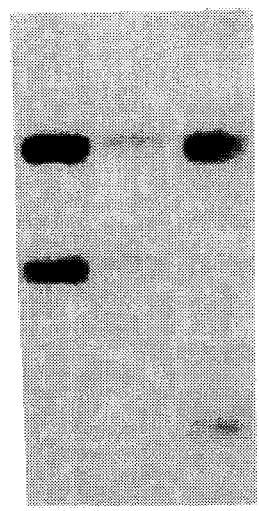
FIG. 3 represents the autoradiograph as described in Example IX.

Using the procedures of Example VI, a mother, child and putative father were tested using the subject invention. FIG. 3 shows a picture of the autoradiogram obtained using pLM 0.8 as a probe against Taq 1 cut DNA obtained from the mother, child and father. Measurement of migration distances and comparison with known standards indicated that the mother carries pLM 0.8-alleles number 7 and 8, the child carries pLM 0.8-alleles number 7 and 8 while the putative father carries pLM 0.8-alleles numbers 2 and 8. Since the mother could have contributed either pLM 0.8 allele number 7 or 8 to the child one can only conclude that the father must have contributed either allele 7 or 8. One can compare the chance that putative father would contribute either pLM 0.8 allele 7 or 8 to a child vs the chance that a random man would contribute either of these alleles. In this case the likelihood ratio is 3.55 which corresponds to a chance of paternity of 71.8%.

TABLE I

Frequency of alleles visualized using pAW101 as a probe and EcoR1 cut human genomic DNA in a population of 298 random individuals.

| Allele # | Size (in kilobase pair) | Frequency |
|---|---|---|
| 1 | 14.0 | 0.013 |
| 2 | 14.5 | 0.052 |
| 3 | 14.9 | 0.077 |
| 4 | 15.4 | 0.117 |
| 5 | 16.0 | 0.146 |
| 6 | 16.6 | 0.117 |
| 7 | 17.2 | 0.064 |
| 8 | 17.7 | 0.040 |
| 9 | 18.3 | 0.035 |
| 10 | 19.0 | 0.030 |
| 11 | 19.6 | 0.035 |
| 12 | 20.2 | 0.040 |
| 13 | 20.8 | 0.064 |
| 14 | 21.6 | 0.069 |
| 15 | 22.2 | 0.023 |
| 16 | 22.7 | 0.018 |
| 17 | 23.6 | 0.020 |
| 18 | 24.3 | 0.003 |
| 19 | 24.6 | 0.008 |
| 20 | 25.3 | 0.013 |
| 21 | 26.1 | 0.008 |
| 22 | 27.1 | 0.002 |
| 23 | 28.1 | 0.002 |

TABLE 2

Frequency of alleles visualized using pLM 0.8 as a probe and EcoR1 cut human genomic DNA in a population of 268 random individuals.

| Allele # | Size (in kilobase pair) | Frequency |
|---|---|---|
| 1 | 2.35 | 0.089 |
| 2 | 2.65 | 0.580 |
| 3 | 2.75 | 0.041 |
| 4 | 2.95 | 0.009 |
| 5 | 3.08 | 0.123 |
| 6 | 3.40 | 0.007 |
| 7 | 3.70 | 0.123 |
| 8 | 4.09 | 0.018 |
| 9 | 4.30 | 0.007 |

What is claimed is:

1. A method of forensic analysis, not including paternity testing, comprising:

(a) obtaining a first sample containing DNA from an individual organism, said individual organism being a human;

(b) obtaining a second sample containing a quantity of DNA sufficient for restriction endonuclease digestion and DNA hybridization;

(c) isolating the DNA of the first sample;

(d) isolating the DNA of the second sample;

(e) subjecting said DNA in each of the samples to the action of at least one restriction endonuclease thereby forming, in each of the two samples, a set of DNA fragments containing one or more polymorphic genetic regions;

(f) in each of the samples, separating by size the DNA fragments generated in step (e);

(g) in each of the samples, hybridizing the DNA fragments separated in step (f) with at least one probe, wherein said probe is a single locus probe and hybridizes with a DNA fragment containing a polymorphic genetic region;

(h) detecting said hybridized probe; and (i) comparing the size of the hybridized fragments generated from the first sample with the size of the hybridized fragments generated from the second sample, thereby analyzing said sample for forensic purposes.

2. The method according to claim 1, wherein the probe molecule is selected from the group consisting of pAW101 (ATCC 19605) and pLM0.8 (ATCC 19604).

3. The method according to claim 1, wherein the DNA from the second sample is obtained from physical evidence or a crime scene.

4. The method according to claim 3, wherein the probe molecule is selected from the group consisting of pAW101 (ATCC 19605) and pLM0.8 (ATCC 19604).

* * * * *